(12) United States Patent
Kimsey, II

(10) Patent No.: US 9,322,748 B1
(45) Date of Patent: Apr. 26, 2016

(54) TISSUE COLLECTION AND REFINING DEVICE AND METHOD

(71) Applicant: Melbourne Kimsey, II, Danville, CA (US)

(72) Inventor: Melbourne Kimsey, II, Danville, CA (US)

( * ) Notice: Subject to any disclaimer, the term of this patent is extended or adjusted under 35 U.S.C. 154(b) by 0 days.

(21) Appl. No.: 14/488,035

(22) Filed: Sep. 16, 2014

(51) Int. Cl.
| | |
|---|---|
| A61M 1/00 | (2006.01) |
| A61M 39/00 | (2006.01) |
| G01N 1/04 | (2006.01) |
| A61B 17/00 | (2006.01) |
| B67C 11/00 | (2006.01) |

(52) U.S. Cl.
CPC ............... *G01N 1/04* (2013.01); *A61M 1/0001* (2013.01); *A61M 1/0005* (2013.01); *A61M 1/0007* (2014.02); *A61M 1/0023* (2013.01); *A61M 1/0056* (2013.01); *A61B 2017/00969* (2013.01); *A61B 2217/005* (2013.01); *A61M 2202/08* (2013.01); *B67C 11/00* (2013.01)

(58) Field of Classification Search
CPC ................... A61M 2209/08; A61M 2209/082; A61M 2209/084; A61M 2202/0021; A61M 2202/0028; A61M 1/0056; A61M 2202/0071; A61M 1/0017; A61M 2202/08; A61M 2202/09; A61M 2202/095; A61M 2202/0014; A61M 1/0023; A61M 1/0001; A61M 5/00; A61M 1/0005; A61M 2205/75; A61M 1/0007; A61B 10/0045; A61B 10/0051; A61B 10/007; A61B 2010/0074; A61B 2218/001; A61B 2218/007; A61B 2017/00969; B67C 11/00
See application file for complete search history.

(56) References Cited

U.S. PATENT DOCUMENTS

| | | | | |
|---|---|---|---|---|
| 954,161 | A | * | 4/1910 | Best ......................... B67C 11/02 141/310 |
| 4,648,140 | A | * | 3/1987 | Bogusz ............................. 4/654 |
| 4,995,386 | A | * | 2/1991 | Ng ............................ 128/205.19 |
| 5,195,567 | A | * | 3/1993 | Tyree, Jr. ................ B67C 11/02 141/297 |
| 5,647,415 | A | * | 7/1997 | Onders .................... B67C 11/02 141/331 |
| D435,906 | S | * | 1/2001 | Wilkinson et al. ........... D24/121 |
| 6,235,010 | B1 | * | 5/2001 | Wilkinson et al. ............ 604/356 |
| 6,508,987 | B1 | * | 1/2003 | Wilkinson et al. ............ 422/550 |
| 8,100,874 | B1 | * | 1/2012 | Jordan et al. .................. 604/319 |
| 8,172,832 | B1 | * | 5/2012 | Gonzalez ...................... 604/542 |
| 8,361,042 | B1 | * | 1/2013 | Gonzalez ............ A61M 1/0001 604/317 |
| 2002/0058915 | A1 | * | 5/2002 | Wakabayashi ................ 604/319 |
| 2002/0082568 | A1 | * | 6/2002 | Yam ............................... 604/319 |
| 2005/0171495 | A1 | * | 8/2005 | Austin et al. .................. 604/317 |
| 2007/0079898 | A1 | * | 4/2007 | Grover .................... B67C 11/02 141/340 |
| 2011/0104800 | A1 | * | 5/2011 | Kensy et al. .................. 435/325 |
| 2012/0271254 | A1 | * | 10/2012 | Schafer et al. ................ 604/319 |
| 2012/0305125 | A1 | * | 12/2012 | Nirmel .................... B67C 11/02 141/1 |
| 2013/0324966 | A1 | * | 12/2013 | Park et al. ...................... 604/506 |

* cited by examiner

*Primary Examiner* — Adam Marcetich

(57) ABSTRACT

A tissue refining device for collecting and processing tissue received from a harvesting device under suction from a vacuum source comprising an improved canister and separator device wherein the canister is reinforced to avoid cracking, an eccentric funnel is used to separate the space within the canister which also allows for visual inspection and control of the tissue, liquid, and fat. A specially designed barbed spout on the funnel allows for flex at that connection without loss of device integrity. The device also has a proprietary method for placement on its custom stand.

6 Claims, 4 Drawing Sheets

TISSUE COLLECTION AND REFINING DEVICE AND METHOD

FIELD

The present invention relates to fluid and tissue collection devices and more specifically to devices for collecting and processing aspirated adipose tissue for use in autologous adipose tissue implantation procedures.

BACKGROUND OF THE INVENTION

Liposuction, a popular type of cosmetic surgery also known as lipoplasty, liposculpture and suction assisted body contouring, is a technique for removing adipose tissue by inserting a hollow tube, or canula, through the skin and connecting it to a vacuum pump to suction out a quantity of fatty tissue. The procedure may be used to remove unwanted deposits of excess fat, to improve body appearance, and to smooth irregular or distorted body shapes, also known as body sculpting. Liposuction may be useful for contouring almost any area of the body including under the chin, neck, cheeks, upper arms, breasts, abdomen, buttocks, hips, thighs, knees, calves, and ankle areas.

A liposuction machine and special instruments are used for this type of surgery. In general, the surgical team first preps the operative site and administers either local or general anesthesia. Through a small skin incision, a suction tube with a sharp end is inserted into the fat pockets and swept through the area where fat is to be removed. The dislodged fat is vacuumed away through the suction tube and deposited into a collection or waste canister. A vacuum pump or a large syringe generates the negative pressure to aspirate the fatty tissue.

In addition to removing unwanted fat, the harvested fat may be re-introduced back into the patient. This is referred to as adipose tissue transplantation. It is preferred to use the patient's own fatty tissue (autologous adipose tissue implantation) since it is more likely to be accepted. Using the patient's own tissues also reduces or even eliminates the need for testing for allergic reactions and the filling replacement tissue may be permanent. Given the decline and drawbacks in the use of foreign substances such as synthetic materials like silicone and Teflon as well as the use of foreign tissues such as bovine collagen, and the advantages of autologous adipose tissue, the interest in and demand for this autologous adipose tissue transplantation continues to increase.

Autologous adipose tissue (or fatty tissue) transplantation is performed by many surgeons for various cosmetic and reconstructive procedures, particularly those relating to the face, hands and other areas. More specifically, autologous fat transplantation involves retrieving adipose tissue using liposuction techniques from an area of abundance and then re-injecting the harvested adipose tissue into a different site of the same individual for cosmetic/reconstructive augmentation or enhancement purposes. Generally, prior to the re-introduction of the tissue into the patient, the adipose tissue must be processed or cleaned to maximize the chances of implant survival. Such processing is preferably accomplished while minimizing the exposure of the tissue to air as possible. However, the adipose cells are relatively delicate and the number of steps and length of time required to separate and process the harvested tissue prior to re-introduction into the patient contributes directly to the success of the operation and decreases the likelihood the tissue will be rejected.

The more commonly used aspiration based liposuction techniques include Tumescent Liposuction, Wet and Super-Wet Liposuction, and Power-Assisted Liposuction (PAL). Tumescent liposuction is the most common type of liposuction. It involves injecting a large amount of medicated solution into the areas before the fat is removed. Frequently, the solution may be up to three times the volume of fat to be removed. The fluid is a mixture of local anesthetic such as lidocaine, a drug that contracts the blood vessels such as epinephrine, and an intravenous (IV) salt solution. The lidocaine in the mixture helps to numb the area during and after surgery, and may be the only anesthesia needed for the procedure. The local anesthesia also contributes to the tumescence (swollen and firm) of the target fat. The epinephrine in the solution helps reduce the loss of blood, the amount of bruising, and the amount of swelling from the surgery. The IV solution helps remove the fat more easily and it is suctioned out along with the fat. This type of liposuction generally takes longer than other types. Less blood is also extracted along with the fat over the wet and super-wet techniques.

The wet and super-wet techniques are similar to tumescent liposuction. The difference is that not as much fluid is used during the surgery—the amount of fluid injected is equal to the amount of fat to be removed. This technique takes less time; however, it often requires sedation with an IV or general anesthesia. Surgical blood loss is less for the super-wet technique than the wet technique but still more than the tumescent technique.

Power-assisted liposuction uses an electric variable speed motor to generate a reciprocating motion and move the canula back and forth in a way that mimics the movement made by a surgeon. It decreases the effort required and allows easier fat extraction.

Unfortunately, the nature of liposuction procedures preclude easy tissue isolation after initial harvest, especially on a large scale, because the volume and/or viscosity of the extracted liposuction effluent also contains unwanted components such as oil, blood and anesthetic solution. Currently, there are no standard techniques, methods, or devices that exist for the simple, large scale isolation and refinement of liposuction-harvested adipose tissue. Although a number of specialized cannulae, needles and methods for tissue harvest and preparation exist, these techniques are tedious and inefficient. Often, the harvested fat is introduced into a centrifuge further traumatizing the fat and adding more steps to the process before the adipose tissue is re-injected back into the patient. As a result, centrifuge-free processes have been developed.

One example of a centrifuge-less system may be found in U.S. Patent Application Publication No. US2006/0093527 to Buss. In general terms, the Buss harvesting and irrigation device is in the form of a syringe housing open on both ends and constructed to receive a removable filter chamber that slides within the housing. One end of the housing may be coupled to a conventional harvesting canula. The housing may form an airtight chamber for holding a vacuum pressure. The tubular filter chamber includes a porous surface and is supported within the housing and spaced apart from the interior wall of the housing so that fluid may flow freely through the filter chamber and along a space between the outer filter chamber and the inner surface of the housing. The filter is sized to contain a majority of fat cells aspirated into the filter from a lumen in the chamber. Fluids for washing the harvested fat cells may be aspirated through the harvested material and out through the porous material while holding the fat tissues within the filter chamber. While this device does provide some advantages over prior solutions and may be suitable in some situations, there are a significant number of components that must manufactured and assembled to construct the device as well as a considerable amount of personal manipulation of the syringe plunger needed to perform the procedure. This includes several plunger retractions and depressions in order to fully pack fat into the syringe housing and also to draw in irrigation fluids to complete the process. This adds to the complexity of the overall training process as well.

Another example may be found in U.S. Patent Application Publication No. US2007/0225686 to Shippert. In general terms, the Shippert tissue transplantation apparatus includes a collection vessel interconnected to a harvesting canula. The vessel defines a chamber in which a series of tissue collecting syringe bodies are coupled to a manifold also in connection with the harvesting canula to provide multiple filling stations. Each syringe body is perforated to retain fatty tissue in the syringe body while allowing other smaller tissues to exit the syringe body. The chamber is also connected to a vacuum source to draw tissue from the canula into the manifold and on into one or more of the syringe bodies. Under the same vacuum, some of the extraneous tissue is drawn out of the syringe bodies leaving fatty tissue behind. Once the desired quantity of fatty tissue is collected, a syringe body may be disconnected from the manifold mount. However, an additional sleeve is required to slip over the outer surface of the syringe body to form a sleeve or protective shell and seal before the syringe may be used. Otherwise, the fatty tissue would simply extrude out of the perforated syringe body as the plunger was depressed.

In another variation of the Shippert system, the harvested tissue is first directed into a tissue washing reservoir containing a fluid bath. However, the entry and exit ports are both provided on the lid of the reservoir and, as explained in Shippert, the washing reservoir must be tipped over onto to its side so as to cover the exit port with washed tissue to allow the washed tissue to be suctioned from the tissue washing reservoir into a manifold in communication with the perforated syringe bodies.

Yet another variation described in the Shippert publication reveals the use of a collapsible filter bag within a collapsible collection bag held within the collection canister to receive fatty tissue from the harvesting device. The filter may be used to separate out fatty tissue into the interior of the collection bag from other fluids under suction also introduced into the collection bag. However, in order to access the fatty tissue in the filter bag, the bag must be removed from the canister and the collection bag manipulated to decant unwanted fluids. If washing the tissue is desired, the collection bag is re-introduced into the canister and a fluid additive is added while the bag is massaged by hand to mix and rinse the fatty tissue. Transferring the collected fatty tissue into a syringe involves forcing tissue through an upper port in the collection bag into a syringe body. While providing a useful multi-stage filling station, the number of steps using these shipped devices results in a cumbersome harvesting and re-injection process that may be improved upon.

While primarily used for tissue specimen collection, another solution for separating tissue may be found in U.S. Pat. No. 5,624,418 to Shepard. In Shepard, a collection and separation device is disclosed that includes a fluid collection container having a lid with a fluid/tissue inlet port and a fluid outlet port that may be coupled to a suction source and a tissue harvesting device. The container also includes a pair of ribs with a lower positioning ledge upon which a pair of tissue collection baskets or traps are positioned above the bottom of the container. While the bottom surface of the container is solid throughout, each basket includes a plurality of fluid flow apertures through which body fluids may pass through while retaining larger tissue specimens in the basket. Fluid collected below the baskets is suctioned up through the fluid outlet port to drain the container, except for the tissue specimens remaining in the baskets. The lid may also be rotated to align each basket with the entry port. However, there is no means to access the collected tissue specimens with first removing the lid resulting in an increased exposure to the surrounding air. The baskets may also be removed for further tissue analysis.

In another variation in Jordan U.S. Pat. No. 8,366,694, which derives itself from the Applicant's own parent U.S. Pat. No. 8,100,874, the addition of concentric tubes to create a pressure equalization within the canister resolves only one of the known issues relating to cracking or implosion of the canisters during procedure, and does not resolve the improvements contained in the invention herein. In Jordan, the seemingly obvious modification of adding concentric tubes within the canister fails to address placement issues and visibility by the user, flexibility and mobility of the funnel, reinforcement of the canister itself, placement, fixation, and barbed structure of the spout, and a myriad of other considerations not addressed in Jordan.

Despite these solutions to date, the need remains for an efficient, simple to use, low cost manufacture and assembly tissue collection and processing device that reduces the trauma to harvested tissue, improves the amount of useful tissue, and maintains a sterile processing environment. Over time, and with considerable use of tissue collection devices in the present art, the data Applicant has collected results in the improved tissue collection and refining device and method herein.

THE INVENTION

Summary, Objects and Advantages

In accordance with the principles of the present invention, a preferred embodiment of a tissue refining device for collecting and processing tissue received from a harvesting device under suction from a vacuum source may comprise a canister body with a reinforced flanged perimeter edges including a vacuum port and an evacuation port operable to be placed in communication with the vacuum source, a tissue harvesting port operable to be placed in communication with the harvesting device and to direct a quantity of tissue retrieved by the harvesting device into the canister body when suction is applied to the vacuum port by the vacuum source, and a tissue retrieval port, and an eccentric separator element with a barbed spout dividing the canister body into an upper vacuum chamber in communication with the vacuum port and the tissue harvesting port and a lower vacuum chamber in communication with the evacuation port, the separator element including a plurality of apertures projecting through the separator element and a depression with a channel in communication with the tissue retrieval port.

The canister itself has extended and flanged perimeter edges for reinforcement, stability and ease of use, with a small indentation opposite the funnel spout orifice for ease of mounting on its stand. On the bottom of the canister, gaps in the flanged edge provide two slot insertion points whereby there is a grip on the flange while also preventing rotating movement of the canister. A plate support resides under the bottom of the canister creating structural support, while still providing maximum available view of contents of the canister and elevation to provide easy access to the barbed spout.

In another feature of the present invention, the separator is in the form of an eccentric funnel with a downwardly extending barbed spout extending the tissue retrieval port outside of the canister body and providing an attachment surface for different types of tubing according to clinical need. The funnel has a specifically designed reinforced circumferentially barbed spout in the design of a hose barb, designed to fit and glue specifically within a similarly reinforced ring around the orifice through which the spout protrudes. In this way, the adhesive adheres specifically and most strongly to the spout itself, the strongest component of the funnel. In this way, the funnel if necessary can flex and move up and down as the canister flexes under vacuum, but the funnel does not lose its position at its strongest and most critical point. The eccentric funnel places the spout more proximal to the edge of the canister versus in the middle. Using this positioning, the users can more easily view the extraction and separation of tissue and fluid, and determine if there is a need to aspirate or plunge the more solid or clogging tissue. Previous designs do not allow this key visibility and thus greatly improved processing method, which also provides the desired alternative to not use tubing at all, but drain directly to another basin, as some surgeons prefer. Additionally, when tubing is attached to this spout and sometimes needs to be added or extracted, it can be done more easily and under visual control as it's near the peripheral edge of the canister. Presently in the field some surgeons have canisters on a table's edge, and place other containers under the spout. This has not been possible with the spout in the middle underneath the canister as with the prior art. In the inventive device, the placement of the spout on the outside edge makes container position more secure, more convenient, and more easily controlled.

In a related feature of the present invention, the spout has small orifices surrounding its upper perimeter to enable thinner fluids like saline to pass through, while not permitting thicker fluids like fat to pass through. Fat will thus pass through the central orifice of the funnel spout, not the small orifices surrounding the upper perimeter of the spout. Those small orifices are designed to be close to the bottom of the canister so they enable the thinnest fluids to evacuate even within the funnel as the thin fluids under the funnel are similarly evacuated. The evacuated fluids are extracted via a tube running from below the funnel to an uppermost lid port where it is connected to evacuation vacuum, extracting fluids when appropriate.

Another aspect of the present invention is a reinforced orifice at the opposite end of the eccentric funnel which is symmetrically placed opposite the funnel spout, and provides the necessary chamber equalization to enable fluid to be evacuated from under the funnel.

BRIEF DESCRIPTION OF THE DRAWINGS

The invention is described in further detail by reference to the drawings in which.

DETAILED DESCRIPTION, INCLUDING BEST MODES OF CARRYING OUT THE INVENTION

Figure 1:
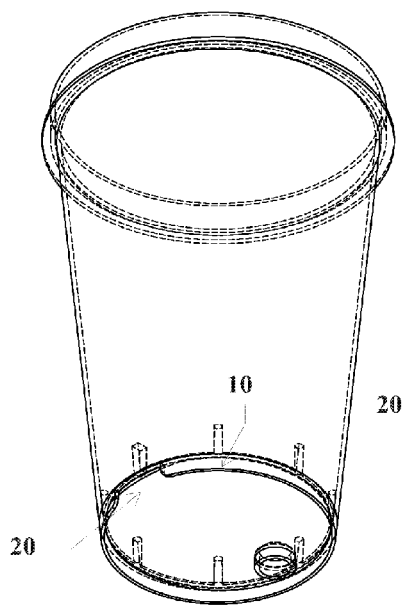
FIG. 1; is an opaque side angle perspective showing the extended and flanged perimeter edges and cut-out of the tissue collection canister by itself, without the inserted funnel, but with the reinforced, flanged orifice for the funnel spout.

Regarding FIG. 1, the opaque representation of the tissue collection canister has extended and flanged perimeter edges 10 for reinforcement, stability and ease of use, with a small indentation 20 opposite the funnel spout orifice for ease of mounting. The canister itself is most often mounted on a stand for improved stability to elevate the funnel spout and the tubing attached to it. Alternatively, some surgeons like to place the canister on the edge of a table or similar plain, and let the fluid run out into another vessel. This has been a request of one of the foremost surgeons in the field, but has not be possible with the funnel spout in the middle bottom of the canister.

Figure 2:
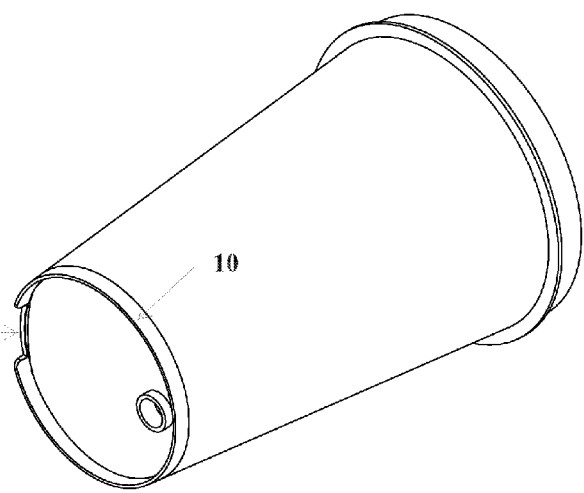
FIG. 2; is a transparent perspective illustrating the extended and flanged perimeter edges and cut-out of the tissue collection canister as above, with bottom view of flanged orifice for the spout.

Regarding FIG. 2, the illustration is transparent in an effort to clearly show the extended and flanged perimeter edges 10 for reinforcement, stability and ease of use, with a small indentation 20 opposite the funnel spout orifice for ease of mounting. Prior art canisters have unreinforced circumferential perimeter edges which add no integrity to the canister, are capable of cracking and imploding, and do not have a reinforced, flanged orifice for the funnel spout itself. Moreover the center location of the bottom of the canister is the single weakest location on a canister when it is under vacuum and flexing. This is because that center bottom is the 'gate' location, where the plastic is inserted into the mold; thus center mounted funnels have exacerbated the weakness by employing a drilled hole for the center-mounted funnel spout. Prior art canisters fail to address any of the vulnerability in the manner the inventive refining device has.

Figure 3:
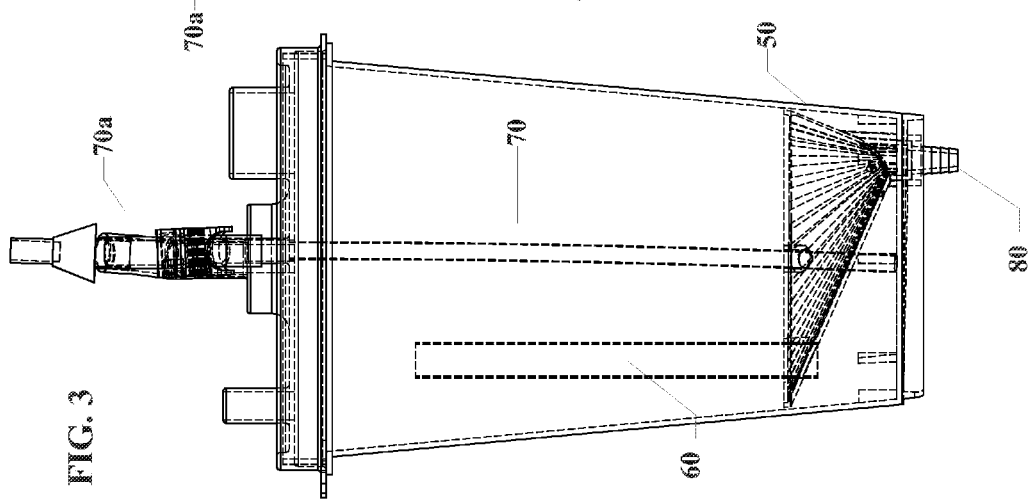
FIG. 3; Canister with the eccentric funnel in place, showing the barbed spout through the flanged orifice, the evacuation tube through the flanged orifice in the upper region of the funnel, and the equalizing orifice opposite the location of the barbed spout.

Regarding FIG. 3, the eccentric funnel 50 is shown mounted, with the evacuation tube or port 70 in place wherein the suctioned fat may be deposited into a collection or waste canister via the vacuum port 70a. The equalization tube 60 is connected opposite the barbed spout in the funnel 80.

Figure 4:
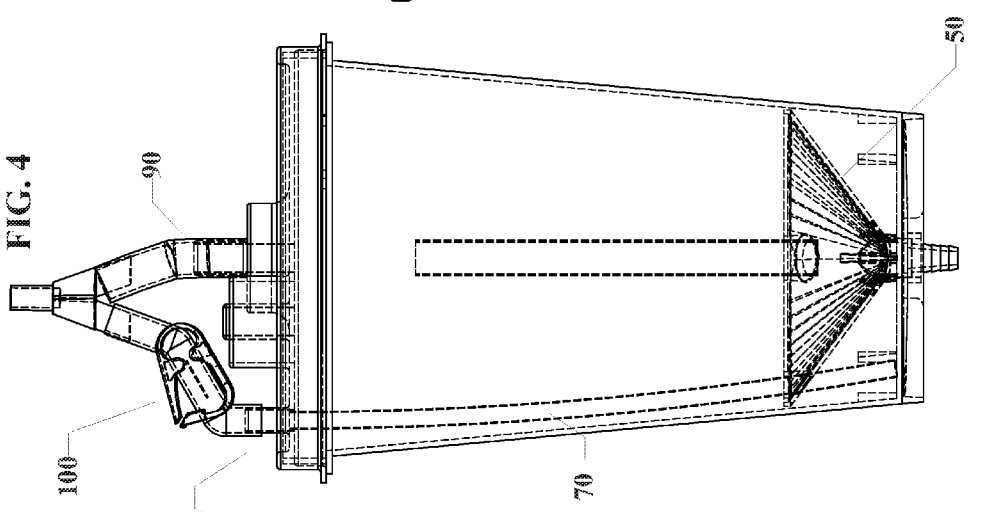
FIG. 4; An alternate angle of the funnel in place, with tubing, ribbed and flanged reinforcement of the canister bottom, and connections to the lid.

Regarding FIG. 4, the Applicant's existing patented connections to the lid (U.S. Pat. No. 8,100,874) are shown as would normally be affixed 90 to effect the suction and evacuation processes. A clamp 100 provides control over the evacuation from fluid from the bottom of the canister where it collects below the separator funnel 50.

Figure 5:
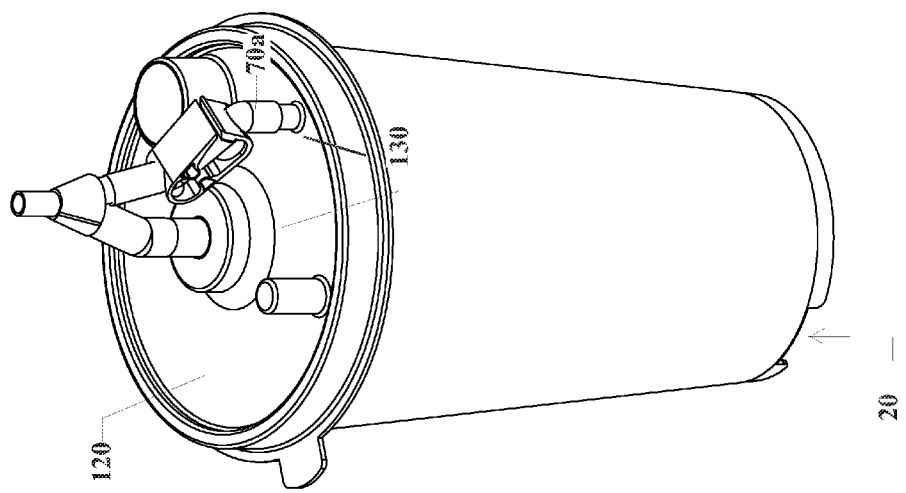
FIG. 5; A top view of the canister lid illustrating tubing connections and evacuation orifices.

Regarding FIG. 5, a top perspective of the canister lid 120 illustrates the locations of the orifices for the tube attachments 130 and the vacuum port 70a. The notch 20 in the canister 140 is also shown and as described previously, aid in holding the canister firmly in a stand.

Figure 6:
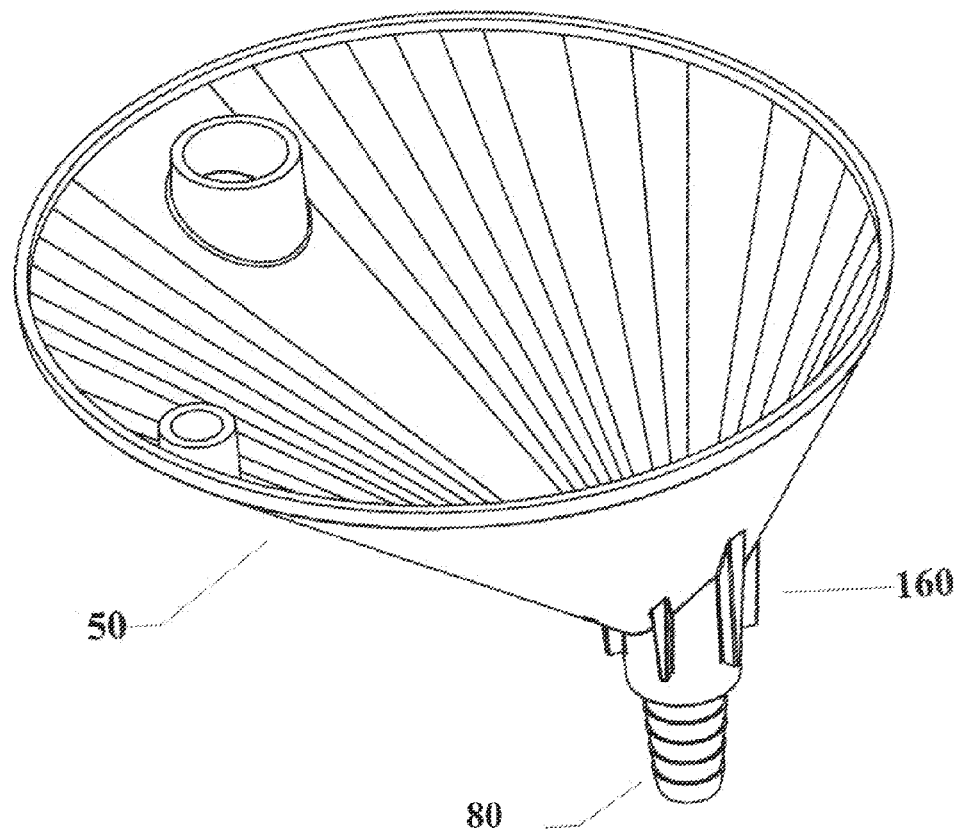
FIG. 6; is a detailed perspective showing the eccentric shape of the separator funnel and separator funnel outlet port and the barbed spout.

Regarding FIG. 6, the funnel 50 has a downwardly extending barbed spout 80 extending the tissue retrieval port outside of the canister body and providing an attachment surface 170 for different types of tubing according to indicated need. This reinforced circumferentially barbed spout in the design of a hose barb, is designed to fit and glue specifically within a similarly reinforced ring around the orifice through which the spout protrudes (not shown in this Figure). In this way, the adhesive adheres specifically and most structurally sound to the spout itself; which is the strongest component of the funnel. This mounting method provides for the probability of twist and vertical movement as the canister flexes under vacuum. The funnel does not lose its position at its strongest and most critical point, which also bolsters canister integrity and avoids procedure failure or abortion due to improperly responding equipment. Whether barely detectable, any such movement with a vessel under vacuum can threaten the integrity of the canister which is simply molded plastic.

Figure 7:
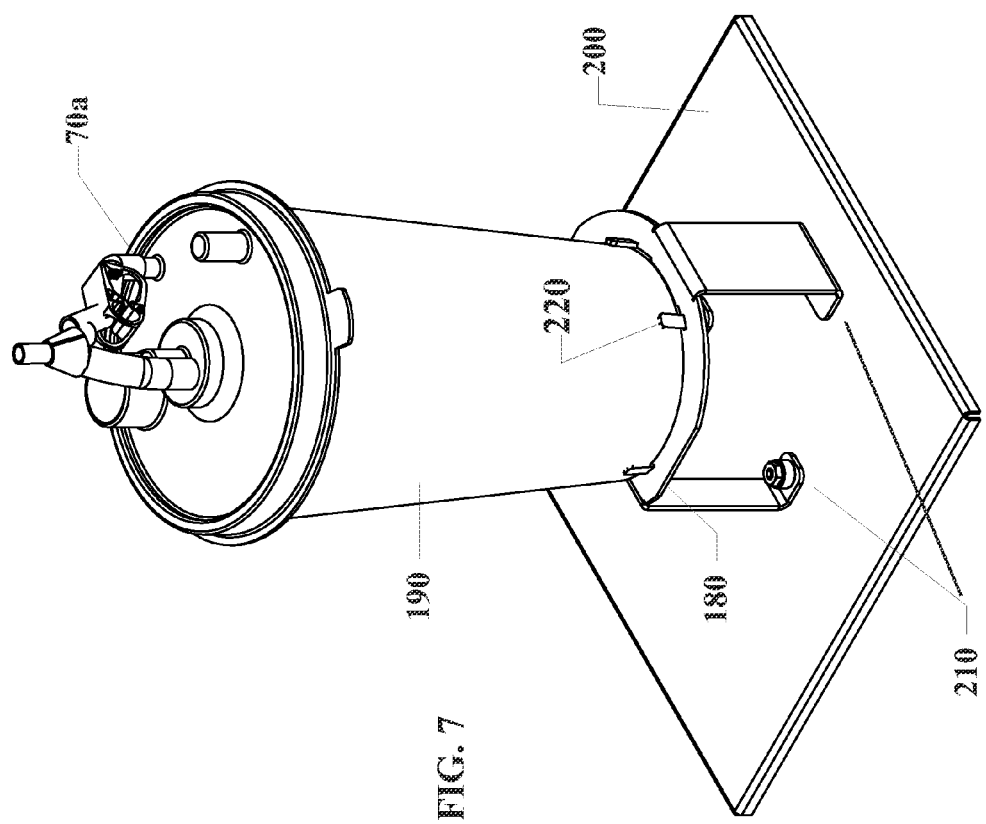
FIG. 7; illustrates the canister in its proprietary stand as mounted on its support plate.

Regarding FIG. 7, the stand 180 is shown with the canister 190 in situ. The mount support plate 200 allows for connection of the stand and further to a pole or method of heightening the canister and stand placement if a surgeon so desires. Stand mounting brackets 210 are a uniform piece of the stand body. The vertical tabs 220 are integrated in the stand and hold the canister in place.

Figure 8:
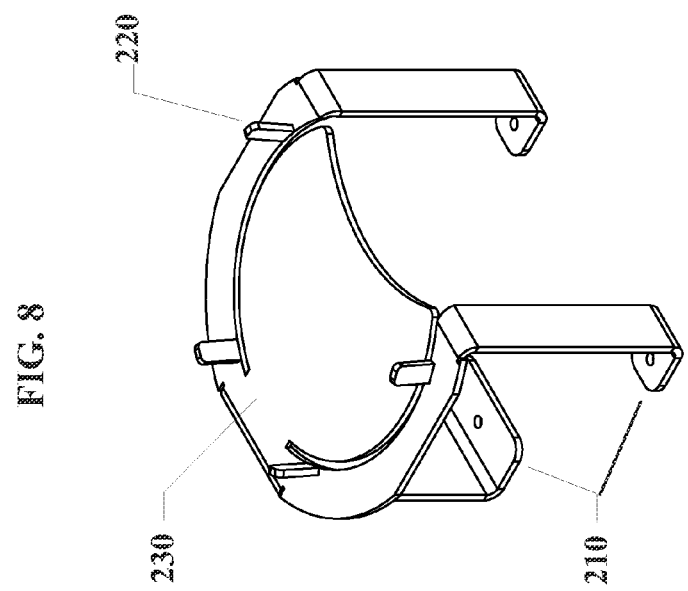
FIG. 8; shows the stand in full view without the canister so as to illustrate the bracketing and connection details.

Regarding FIG. 8, the stand alone is shown to illustrate the receiving notch 230 wherein the canister affixes front, and the mounting brackets 210 are clearly visible wherein they will bolt to the support plate as in FIG. 7. The vertical tabs 220 serve to hold and support the canister in place.

The invention claimed is:

1. An improvement to a device for collecting and refining tissue received from a harvesting device under suction from a vacuum source, comprising: a canister body with reinforced perimeter edges containing a scored notch, an eccentric separator element dividing the canister body into an upper vacuum chamber in communication with the vacuum port and the tissue harvesting port and a lower vacuum chamber in communication with the evacuation port, the separator element including a plurality of apertures projecting through the separator element and a depression with a channel in communication with the tissue retrieval port; the eccentric separator element having a reinforced barbed spout attachable to the extending the tissue retrieval port outside of the canister body and providing an attachment surface for different types of medical tubing wherein the scored notch extends along a circumferential region facing opposite the barbed spout.

2. A device as in claim 1 wherein the canister has extended and flanged perimeter edges for added structural integrity of the canister.

3. A device as in claim 1 wherein the canister has a small indentation or notch opposite the funnel spout orifice for ease of mounting on a stand.

4. A device as in claim 1 wherein the separator element is an eccentric funnel proximal to the edge of the canister with a downwardly extending circumferentially barbed spout extending the tissue retrieval port outside of the canister body and providing an attachment surface for different types of tubing, and wherein the barbed spout is a hose barb.

5. A funnel as in claim 4 wherein the funnel spout has small orifices surrounding its upper perimeter to enable thinner fluids like saline to pass through, while not permitting thicker bodily fluids including fat to pass through.

6. A device as in claim 1 wherein the orifice through which the funnel spout is designed to fit and glue specifically within a reinforced ring around the orifice wherein the reinforced ring is fixed to the spout itself, aiding in the structural integrity and flexibility of the spout.

* * * * *